United States Patent [19]
Sullivan et al.

[11] Patent Number: 5,746,753
[45] Date of Patent: May 5, 1998

[54] NEEDLE GRASPING APPARATUS

[75] Inventors: Roy H. Sullivan, Uxbridge; Barry N. Gellman, North Easton, both of Mass.

[73] Assignee: Boston Scientific Corporation, Natick, Mass.

[21] Appl. No.: 645,173

[22] Filed: May 13, 1996

[51] Int. Cl.[6] .................................................. A61B 17/04
[52] U.S. Cl. ........................ 606/147; 606/144; 606/148
[58] Field of Search ................................... 606/144, 147, 606/148, 151, 209, 205, 206, 208, 207

[56] References Cited

U.S. PATENT DOCUMENTS

| | | | |
|---|---|---|---|
| 3,878,848 | 4/1975 | Hiebert | 128/334 |
| 4,109,658 | 8/1978 | Hughes | 128/340 |
| 4,446,866 | 5/1984 | Davison | 128/340 |
| 4,491,135 | 1/1985 | Klein | 128/340 |
| 4,597,390 | 7/1986 | Mulhollan et al. | 128/340 |
| 4,621,640 | 11/1986 | Mulhollan et al. | 128/340 |
| 4,793,349 | 12/1988 | Weinrib | 128/340 |
| 4,800,880 | 1/1989 | Catalano | 128/340 |
| 5,015,250 | 5/1991 | Foster | 606/147 |
| 5,181,919 | 1/1993 | Bergman et al. | 606/144 |
| 5,201,744 | 4/1993 | Jones | 606/144 |
| 5,222,962 | 6/1993 | Burkhart | 606/148 |
| 5,281,236 | 1/1994 | Bagnato et al. | 606/139 |
| 5,300,082 | 4/1994 | Sharpe et al. | 606/147 |
| 5,304,185 | 4/1994 | Taylor | 606/147 |
| 5,312,422 | 5/1994 | Trott | 606/144 |
| 5,336,230 | 8/1994 | Leichtling et al. | 606/148 |
| 5,364,409 | 11/1994 | Kuwabara et al. | 606/148 |
| 5,376,096 | 12/1994 | Foster | 606/147 |
| 5,391,174 | 2/1995 | Weston | 606/148 |
| 5,391,176 | 2/1995 | de la Torre | 606/148 |
| 5,413,583 | 5/1995 | Wohlers | 606/206 |
| 5,437,682 | 8/1995 | Grice et al. | 606/148 |
| 5,447,512 | 9/1995 | Wilson et al. | 606/139 |

*Primary Examiner*—Michael Buiz
*Assistant Examiner*—Tina T. D. Pham
*Attorney, Agent, or Firm*—Finnegan, Henderson, Farabow, Garrett & Dunner, L.L.P.

[57] ABSTRACT

Apparatus for needle grasping and performing a second modality comprising a sheath axially extending between distal and proximal ends thereof. The device includes an inner hollow tube with a slot formed therein for receiving a needle at the distal end. Retraction and extension of the inner tubular member relative to the sheath enable the grasping and releasing of a suture needle received in the slot. A handle is provided at the proximal end of the apparatus for selectively extending and retracting the inner tube relative to the sheath and for retaining the inner tube in its extended and retracted positions. A second switch can be provided in the handle to actuate a catheter slidably inserted through the inner tube to perform a second therapeutic modality. The catheter preferably includes a distal bight that forms a loop when extended from the distal end of the sheath for facilitating intracorporeal knot tying thereat. The catheter includes a lumen therethrough for receiving suture thread for use at the distal end of the sheath.

36 Claims, 9 Drawing Sheets

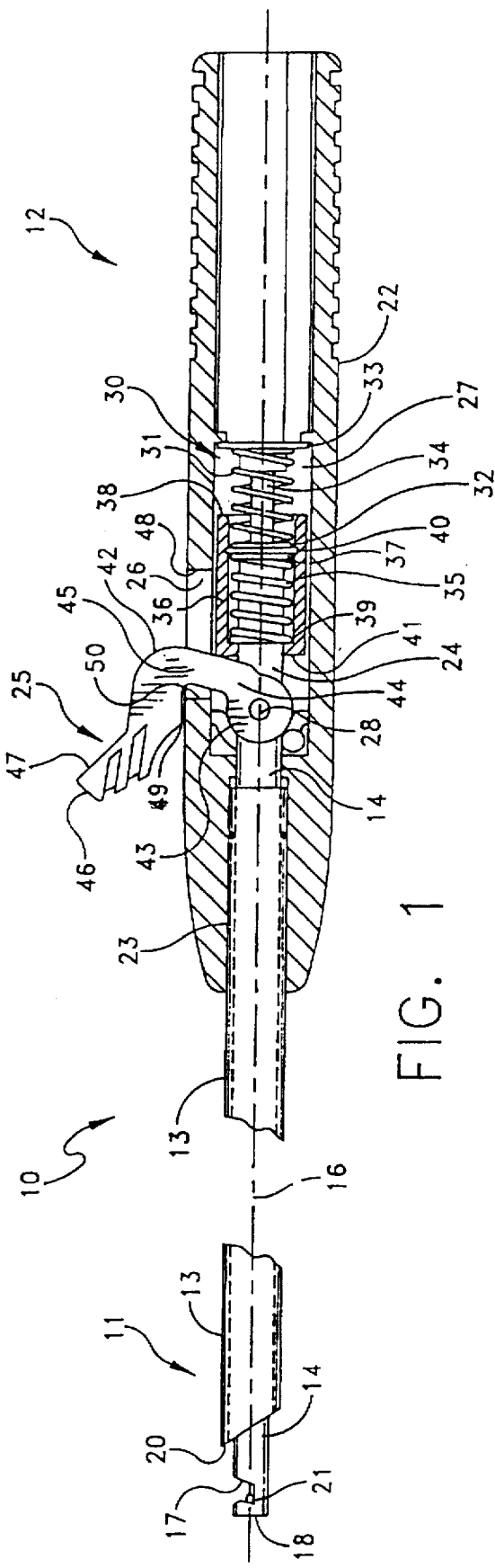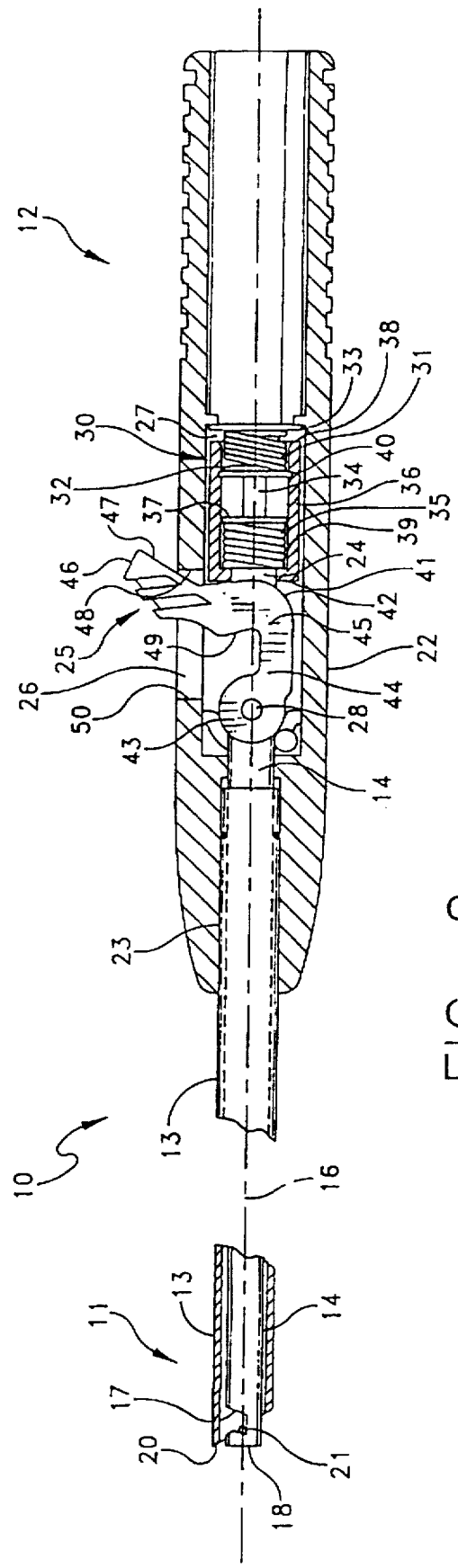

NEEDLE GRASPING APPARATUS

BACKGROUND OF THE INVENTION

1. Field of the Invention

This invention relates to surgical devices and procedures and more specifically to an apparatus for suturing openings in a patient during endoscopic surgical procedures.

2. Description of Related Art

In endoscopic surgical procedures, all the techniques of dissection and suturing, including knot tying, must be performed with various elongated instruments that extend through trocars into a cavity of a patient. These instruments generally include needle holders, tissue graspers, introducers and related instruments for facilitating both extracorporeal and intracorporeal knot tying and suturing during endoscopic surgical procedures. During such endoscopic surgical procedures the needle holders and knot tying devices are generally among the final devices to inserted into and removed from the trocars to suture the patient's tissue.

The following U.S. Pat. Nos. disclose representative needle gripping and driving apparatus for use during endoscopic surgical procedures:

3,878,848 (1975) Hiebert 5,015,250 (1991) Foster 5,300,082 (1994) Sharpe et al.

5,312,422 (1994) Trott 5,364,409 (1994) Kuwabara et al.

5,376,096 (1994) Foster

U.S. Pat. No. 3,878,848 to Hiebert discloses a needle capturing device. This device includes a handle member at one end and a tip in the form of a solid block which may be penetrated by a surgical needle so that manipulation of the handle member permits manipulation of the suture needle penetrating the block.

U.S. Pat. No. 5,015,250 to Foster discloses a needle driver for selectively grasping a suture needle. A cross-channel in an overlying sheath receives the suture needle. A distal end of a slidable inner rod supported within the sheath grips the needle by distally pushing it against a wall of the cross-channel. Proximal manipulation of a handle portion supported at a proximal end of the sheath and the inner rod enables retraction and extension of a distal end of a inner rod relative to the channel for selectively grasping and releasing the suture needle.

U.S. Pat. No. 5,300,082 to Sharpe et al. discloses a surgical instrument having a trigger handle for grasping a needle at a distal end of a tubular member. The distal end includes a cross-notch or channel for receiving the needle whereby an end of the inner tube clamps the needle against a distal end of the notch. The trigger handle includes a latching device that selectively locks the needle members in position when the needle is engaged.

U.S. Pat. No. 5,312,422 to Trott discloses a suturing needle apparatus that includes an elongated handle with a push block that connects with a slide actuated thumb switch. The push block also connects with an elongated needle assembly that extends distally from the handle. The distal end of the needle portion is selectably retractable relative to a distal end of an overlying sheath member to retain a suture in a slot of the needle. A finger switch overcomes a lock feature that inhibits unintended extension of the needle assembly.

U.S. Pat. No. 5,364,409 to Kuwabara et al. discloses a needle holder for gripping a needle within a body cavity. The disclosed device includes an elongated tubular member underlying a sheath. A fixed needle holding element and a movable holding element support at a distal end of the tubular member come together with the fixed element in a scissors-like fashion to grip a needle. An inner core extending from a biased scissors-like handle slides in the tubular member responsive to manipulation of the handle to actuate the movable holding element between the gripping and released positions. The outer surface of the tubular member also includes a suture hook or fixing element to assist in the formation of loops for tying the suture in an overhand knot.

U.S. Pat. No. 5,376,096 to Foster discloses a needle driver for selectively grasping a suture needle. A channel in a distal end of a slidable inner rod supported within an overlying sheath grips the needle in the channel against a distal end of an overlying sheath. Manipulation of a handle portion supported at a proximal end of the sheath and inner rod enables retraction and extension of the inner rod relative to the sheath for selectively grasping and releasing the suture needle.

The following U.S. Pat. Nos. disclose representative apparatus for intracorporeal knot tying in endoscopic surgical procedures:

5,281,236 (1994) Bagnato et al.

5,336,230 (1994) Leichtling et al.

5,391,176 (1995) de la Torre et al.

5,447,512 (1995) Wilson et al.

U.S. Pat. No. 5,281,236 to Bagnato et al. discloses a method and device for intracorporeal knot tying. The device includes a proximal control apparatus, a distally extending, axially stiff sheath, and a distally extending tubular member formed of shaped memory material for carrying a suture thread through a through passage in the tubular member. The tubular member includes a bight formed of a shape memory material at its distal end that upon selective extension from the sheath forms a loop and upon retraction into the sheath returns to a linear extension. When the tubular member is extended from the sheath and a free end of the suture material extends through the tubular member is passed through the loop, retracting the tubular member forms an overhand knot in the suture material. Subsequent tightening of the knot is performed by pulling the suture material proximally through the tubular member while grasping with a grasping device the free end of the suture material.

U.S. Pat. No. 5,336,230 to Leichtling et al. discloses an endoscopic suture tying apparatus that includes a proximal operating section with scissors-like members for external manipulation by a surgeon to control a distal section extending internally of a patient. The distal section comprises first and second hollow tube members having a bore therein and a push/pull rod slidably mounted in the bore of each of the tubular members. The scissors-like member secures to the proximal end of each of the tube members for selectively moving the push/pull rods. The ends of the tube are used to selectively loop suture material and pull the suture material through the loops to knot the suture material.

U.S. Pat. No. 5,391,176 to de la Torre et al. discloses a surgical instrument and method for tying knots in a length of suture material at a remote location. The device includes a hollow tube with suture threads wrapped in axially spaced loops proximate a distal end of the tube. A proximally extending slot at the distal end of the tube underlies the spaced loops. Passing a suture needle secured to the free end of the suture material into the distal end of the tube and out of the slot proximally of the distal most loop forms an overhand knot in the suture material.

U.S. Pat. No. 5,447,512 to Wilson et al. discloses an intracorporeal knot tying device with a proximal controller

3 or handle and a distal portion substantially identical to the distal portion of the device disclosed by U.S. Pat. No. 5,281,236 to Bagnato et al., as described above. The controller includes a housing that supports a slide button for selectively extending and retracting the tubular member relative to the sheath. The slide button also enables the user to engage the suture material as the slide button retracts the tubular member so as to pull one side of an intercorporeal knot formed proximate a distal end of the tubular member.

The foregoing references disclose various apparatus for gripping and driving needles during intracorporeal knot tying. However, they fail to disclose a singular apparatus that enables grasping and driving a needle in order to suture a patient's tissue and that facilitates intracorporeal knot tying to secure the suture. The apparatus disclosed by these references also fail to provide an easily used control apparatus that holds needle grasping members in open and closed positions to positively grasp and release a suture needle when selectively moved to such positions. Further, the references fail to teach a device with a needle grasping apparatus at a distal end and a proximal operating apparatus that controls both the needle graspers and a second catheter extending distally in the device for providing alternative or additional therapeutic modalities of treatment.

SUMMARY

Therefore it is an object of this invention to provide a method and an apparatus for positively retaining suture needle grasping members of the apparatus in selected open and closed positions.

It is another object of this invention to provide needle grasping apparatus that can be used to perform a second modality of therapeutic treatment.

It is yet another object of this invention to provide a needle grasping apparatus that includes a handle for selectively and positively urging grasping members of the apparatus to open and closed positions.

It is still another object of this invention to provide a method and an apparatus for positively and selectively grasping and releasing a suture needle and for performing a second therapeutic procedure.

It is yet still another object of this invention to provide a proximal handle for a needle grasping apparatus that selectively retains distal grasping members of the apparatus in selected open and closed positions and that selectively extends a tubular member relative to the grasping members for performing a second procedure.

It is a further object of this invention to provide a method and apparatus for suturing a patient's tissue with a needle grasping and driving device and facilitating intracorporeal knot tying with the same device.

Accordingly apparatus for facilitating endoscopic therapy according to this invention includes first and second coaxially extending members that are displacable between first and second end positions relative to one another with an intermediate position defined in response to interference between end portions of the coaxial members. A handle attaches to the proximal end portion of the first coaxial member and supports a camming member for moving the coaxial members between first and second positions. A lost motion transfer unit coaxially mounts with the coaxial members and abuts the housing, camming member and the second coaxial member. The lost motion transfer unit responds to motion of the camming member by establishing a first end position when the camming member is in a first position. When the camming member moves to a second position, the lost motion transfer unit establishes the second end position and the intermediate position depending upon the presence of interference at the distal end portions of the coaxial members.

In accordance with another aspect of this invention a needle grasping apparatus with proximal and distal ends for facilitating intercorporeal knot tying of suture material during endoscopic procedures includes first and second grippers proximate a distal end of the apparatus, a catheter extending between the proximal and distal end of the apparatus, and a controller at the proximal end for operating the catheter and the first and second grippers. One of the grippers includes a proximally extending portion. The controller includes a housing that supports a cam member for movement between first and second positions and a cam follower axially displaced from the cam member. A first biasing member of the controller engages the housing and the cam follower and urges the cam follower towards the camming member. A second biasing member of the controller extending between a proximal end of the one gripper and the cam follower urges the cam follower away from the proximal end of the one gripper. The first biasing member thus compresses in response to the motion of the camming member and the second biasing member compresses in response to motion of the camming member when interference exists between the first and second grippers.

BRIEF DESCRIPTION OF THE DRAWINGS

It is intended that the appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a side view in cross section of a needle grasping apparatus according to this invention with a needle gripping member in an extended position for releasing a suture needle;

FIG. 2 is a side view in cross section of a needle grasping apparatus of FIG. 1 with the needle gripping member in an intermediate position for retaining the suture needle;

DESCRIPTION OF ILLUSTRATIVE EMBODIMENTS

Figure 3:
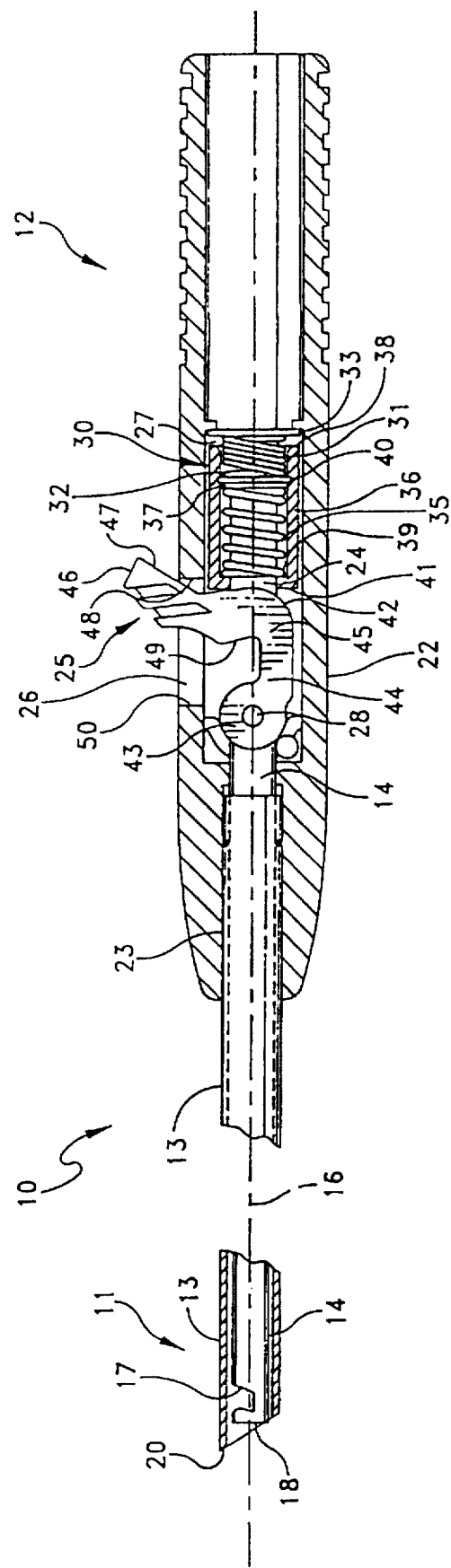
FIG. 3 is a side view in cross section of the needle grasping apparatus of FIG. 1 with the needle gripping member in a fully retracted position without a suture needle.

An apparatus 10 for facilitating intracorporeal suturing of a patient's tissue according to this invention as depicted in FIG. 1 comprises distal and proximal sections 11 and 12, respectively. The distal section 11 includes a sheath 13 and a tubular member 14, each of which extends generally along an axis 16. A transverse slot 17 proximate a distal end 18 of the tubular member 14 and a distal end 20 of the sheath 13 define needle grasping members that, upon relative axial displacement of the tubular member 14 and the sheath 13, operate to release and to grip a suture needle 21 disposed in the slot 17. That is, distal axial displacement of the tubular member 14 relative to the sheath 13 releases the needle 21 as depicted in FIG. 1 where the tubular member 14 is shown in a distally extended position. Proximal displacement either causes the needle 21 to be clamped at the distal end 18 as depicted in FIG. 2 in an intermediate clamping position or causes the tubular member 14 to displace to a proximally retracted position within the sheath 13 as depicted in FIG. 3 if no needle is in the slot 17.

Figure 4:
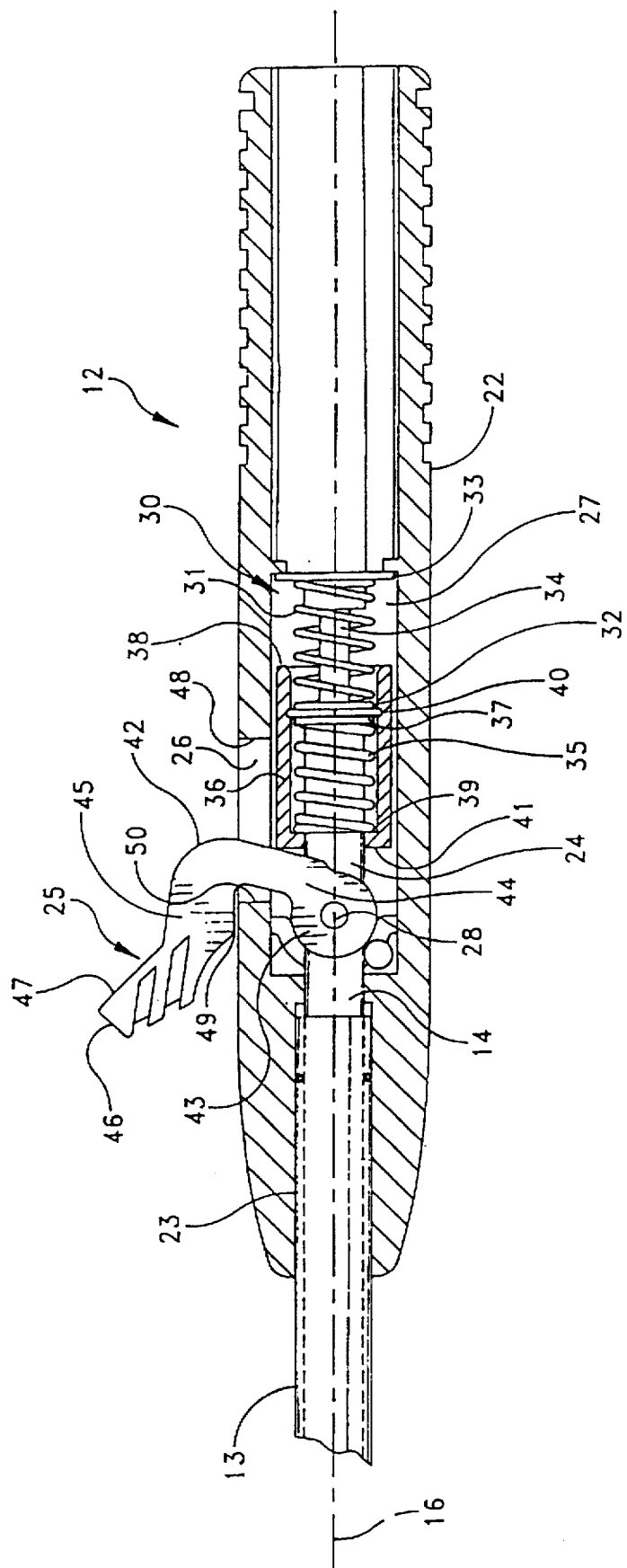
FIG. 4 is an enlarged side view of a handle used in the needle grasping apparatus of FIGS. 1 through 3.

At the proximal section 12 shown in FIGS. 1 through 3, and in an enlarged form in FIG. 4, a handle 22 attaches to a proximal end 23 of the sheath 13 as a first co-axial member and supports a proximal end 24 of the second tubular member 14 as a second co-axial member to enable displacement relative to the sheath 13. The second tubular member 14 thereby can move to its distally extended, proximally retracted or intermediate needle clamping positions. A lever switch or trigger 25 extends through a slot or passage 26 from a cavity 27 in the handle 22. The trigger 25 mounts for rotation on transverse axles or bosses 28 within the housing 27 for movement between first and second limit positions as seen in FIGS. 1 and 2, respectively.

A lost motion transfer assembly 30 enables the two positions of the trigger 25 to translate the tubular member 14 to any of its three positions in a positive fashion. That is, when the trigger 25 is in its fully clockwise position as shown in FIGS. 2 and 3, the inner tubular member 14 will be in its clamping position if a needle 21 is positioned at the distal end thereby to cause interference between the co-axial members or in its fully retracted position if no needle is present. When the trigger is moved counter clockwise to the position shown in FIG. 1, the inner tubular member 14 is in its distally extended position.

Referring specifically to FIG. 4, the lost motion transfer assembly 30 includes a first spring member 31, a central transverse annular flange 32 and a proximal flange 33 that abut the distal and proximal ends of the first spring member 31 respectively, a guide tube 34, a second spring member 35 and a casing in the form of a spring cup 36 positioned to abut the proximal end of the second spring member 35. A flange 37 is formed integrally with the proximal end of the inner tubular member 14. More specifically, the first spring member 31 is co-axially positioned over the guide tube 34 and biases the flange 32 distally away from the tubular flange 33. The guide tube 34 extends into the tubular member 14 to maintain the proximal end 24 on the axis 16 during translation of the tubular member 14. The second spring member 35 is co-axial with the proximal end 24.

The spring cup 36 or casing has a cylindrical shape with an open proximal end 38 and a partially closed distal end 39 that is adapted to slide over the proximal end 24 of the inner tubular member 14. The edge of a flange 40 engages an inner groove in the spring cup 36 displaced slightly proximally from the proximal end 38. The spring 35 thus lies between the distal end 39 of the spring cup 36 and the flange 37. Moreover the spring 31 has a lower modulus than the spring 35.

The distal end 39 of the spring cup 36 or casing is formed with an oblique or skewed transverse surface 41 that interacts with a camming surface 42 on the trigger 25. The trigger 25 has a mounting base portion 43 that rides on the axle 28 and may be further captured and supported by a saddle 44. Typically the trigger base portion 43 will have two spaced mounting portions that straddle the inner tubular member 14. An arm structure 45 that may comprise a common arm or spaced arm portions, extends from the base portion 43 through the slot 26. An actuator or manipulator 46 in the form of a thumb actuator in FIG. 4 enables the displacement of the trigger 25 between its first and second positions.

In this particular embodiment, interference between a surface 47 on the trigger 25 and an outer surface 48 of the handle 22 adjacent the distal end of the slot 26 produces a positive stop or limit for counter clockwise motion of the trigger 25. Interference between a surface 49 on the trigger 25 and a surface 50 on the handle 25 adjacent the proximal end of the slot 26 produces a positive stop or limit for counter clockwise motion of the trigger 25.

Referring now to FIGS. 1 and 4, when the trigger 25 is in its fully counter clockwise position, the spring 31 drives the flange 32 distally to displace the distal end 39 of the spring cup 36 against the camming surface 42. Simultaneously the spring 35 drives the flange 37 and the inner tube 14 proximally until the flange 37 abuts the flange 40. This defines the distally extended position of the inner tubular member 14.

If a suture needle 20 is positioned at the distal end 11 as shown in FIG. 2, a two-phase operation results as the trigger 25 moves to the clockwise stop. Initially no interference exists between the inner tubular member 14 and the sheath 13 so the spring cup 36 moves proximally and compresses the spring 31. The spring 35, due to its higher modulus, remains as shown in FIGS. 1 and 4. When the inner tubular member 14 closes on the suture needle 21, no additional proximal motion of the inner tubular member 14 can occur. As the trigger 25 continues to rotate to the positive stop for clockwise motion, it continues to displace the spring cup 36 in the lost motion transfer assembly 30 and now compresses the spring 31 and begins to compress the spring 35 as the flange 37 remains stationary. When the handle reaches the positive clockwise stop, both the springs 31 and 35 are fully compressed, the handle 25 is in a stable position and the spring 35 produces the clamping force on the suture needle 20 at the distal end of the device. This constitutes an intermediate clamping position.

If no suture needle is present, the trigger 25 moves to the position in FIG. 3. In this position only the spring 31 compresses fully. The spring 35 fully separates the end 41 of the spring cup 36 and the flange 32. The springs 31 and 35 cooperate to urge the skewed surface 41 of the spring cup 36 to bear continuously on the camming surface 42. The camming surface 42 when in each of counter clockwise and clockwise positions is in an over-center position. That is, in FIG. 1 the spring 31 acts to drive the trigger 25 against the counterclockwise stop; in FIGS. 2 and 3, the springs 31 and 35 drive the trigger 25 against the clockwise stop. Consequently no operator force is needed to maintain the trigger 25 in either of these positions.

Figure 5:
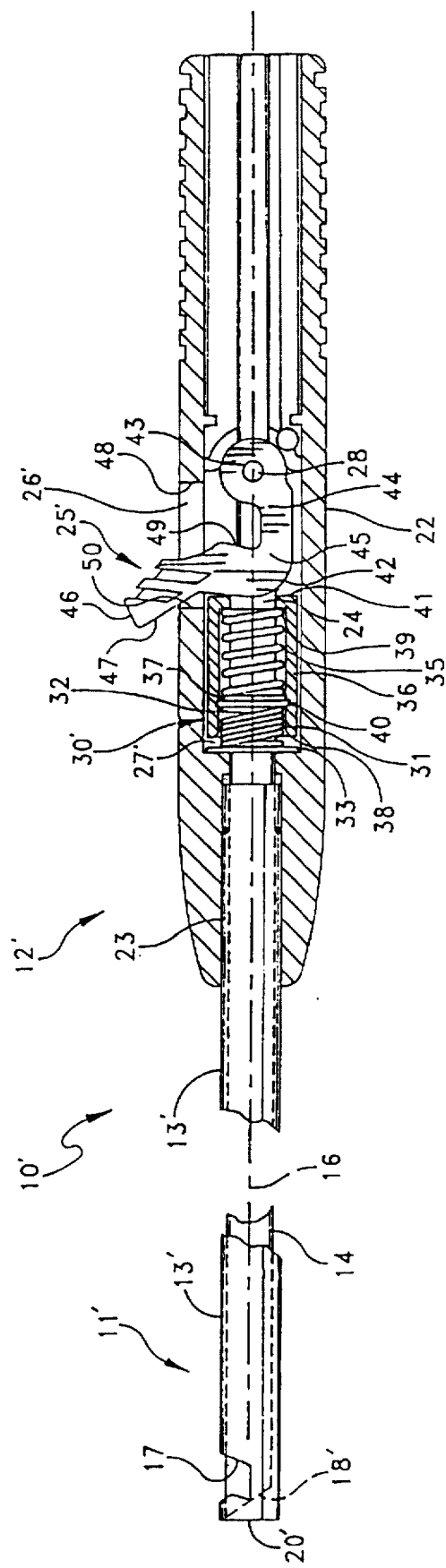
FIGS. 5 through 7 are views of an alternative embodiment of this invention corresponding to FIGS. 1 through 3.
Figure 6:
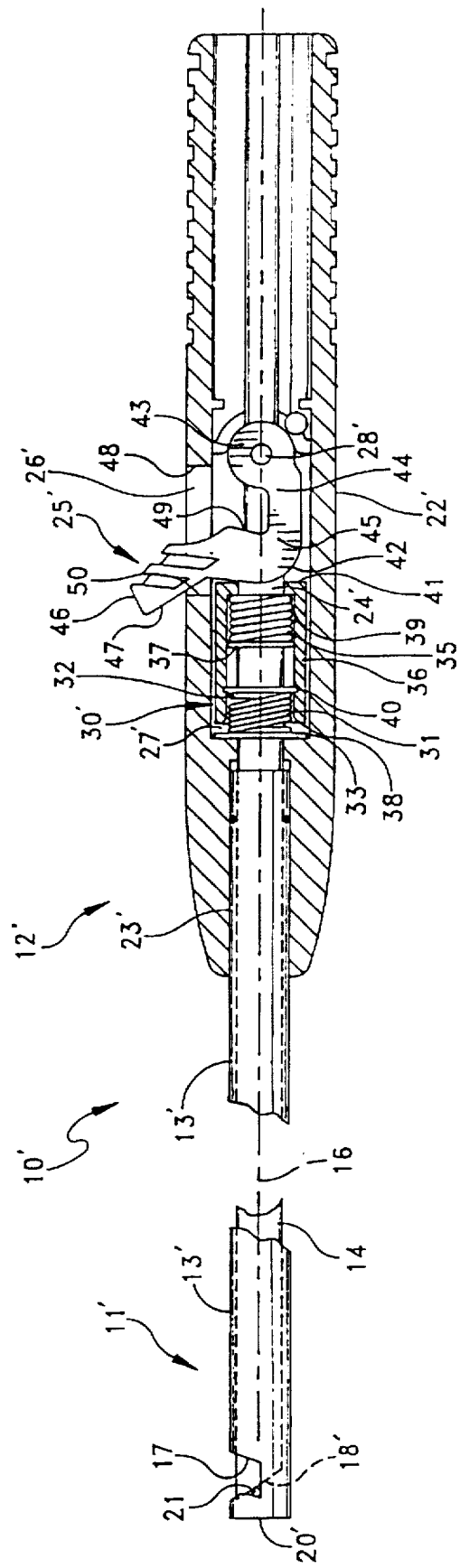
Figure 7:
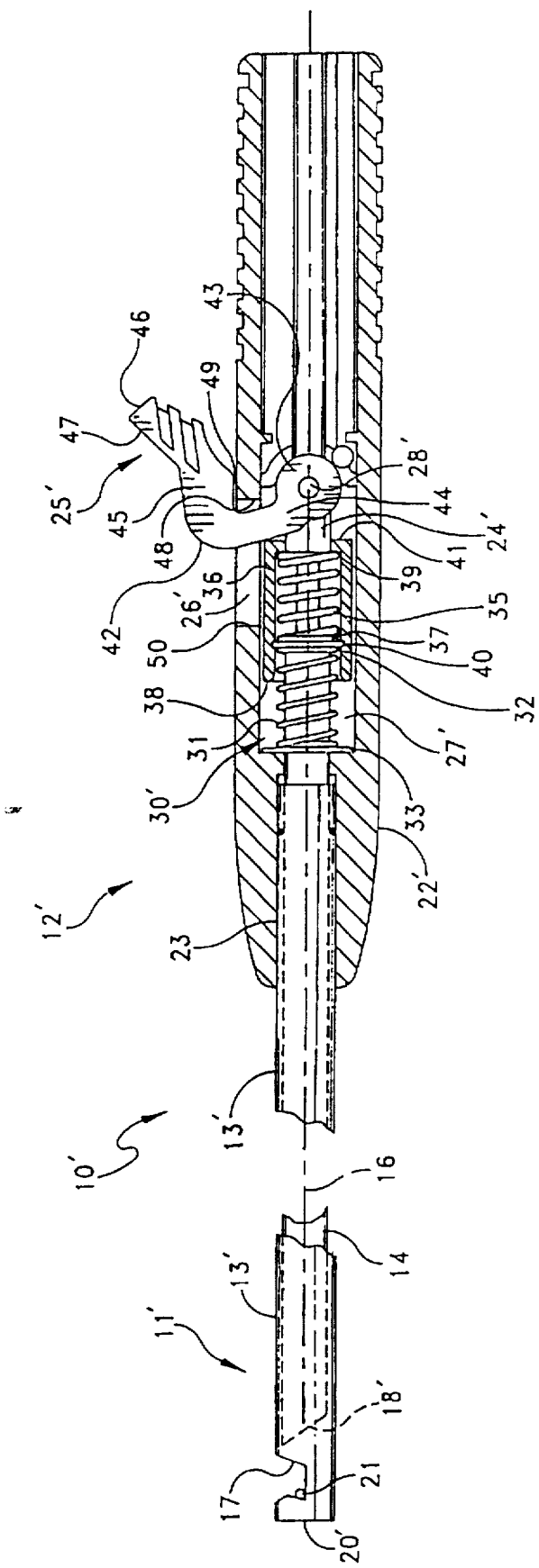

An apparatus 10' for facilitating intracorporeal suturing according to another embodiment as depicted in FIGS. 5 through 7 includes a distal section 11' and the proximal section 12'. The sheath 13' is preferably formed to be slightly longer than an underlying tubular member 14' in this embodiment and it also moves axially in response to proximal manipulation of a handle 22'. A suture needle slot 17' for receiving the suture needle 21 proximate a distal end 20' of a sheath 13'. Proximal axial displacement of the tubular member 14' as depicted in FIG. 7 releases the suture needle 21 and enables the suture needle 21 to be removed from or received in the slot 17'. On the other hand, distal axial displacement of the tubular member 14' grasps the suture needle 21 received in the slot 17' (see FIG. 6) or closes the slot and generally prevents passage of objects into the slot 17' (see FIG. 5) when no interference exists between the sheath 13' and the tubular member 14'.

The handle 22' attaches to a proximal end of the sheath 13' and supports a proximal end 24' of the tubular member 14'. A trigger 25' extends through a slot 26' in the cavity 27' in the handle 22'. The trigger 25' suitably mounted in the handle 22' moves between first and second positions as seen in FIGS. 5 and 6, respectively. A lost motion transfer assembly 30' enables the two positions of the trigger 25' to translate the tubular member 14' to its three positions. That is, as the trigger 25' moves to its distal or clockwise position, the tubular member 14' moves to the clamping position of FIG. 6, if a needle 21 is positioned in the slot 17' or to the position shown in FIG. 5.

The lost motion transfer assembly 30' of FIGS. 5 through 7 includes substantially the same members as the assembly 30 of FIGS. 1 through 4. However, the distal end of the spring member 31 abuts the flange 33, which is positioned distally in the cavity 27'. Also, the proximal end of the second spring member 35 engages the now proximal end 39 of the spring cup 36 while the distal end of the second spring member 35 engages the flange 37 formed integrally with the proximal end of the tubular member 14' and positioned proximally of the central flange 32. Thus, the second spring member 35 overlies a guide tube 34 that extends distally from a proximal portion of the handle 22'. Those skilled in the art will now appreciate movement of the trigger 25' between the first and second positions enable the movement of the tubular member 14' relative to the sheath to its three positions. In the retracted position shown in FIG. 7 both springs 31 and 35 are expanded.

Figure 8:
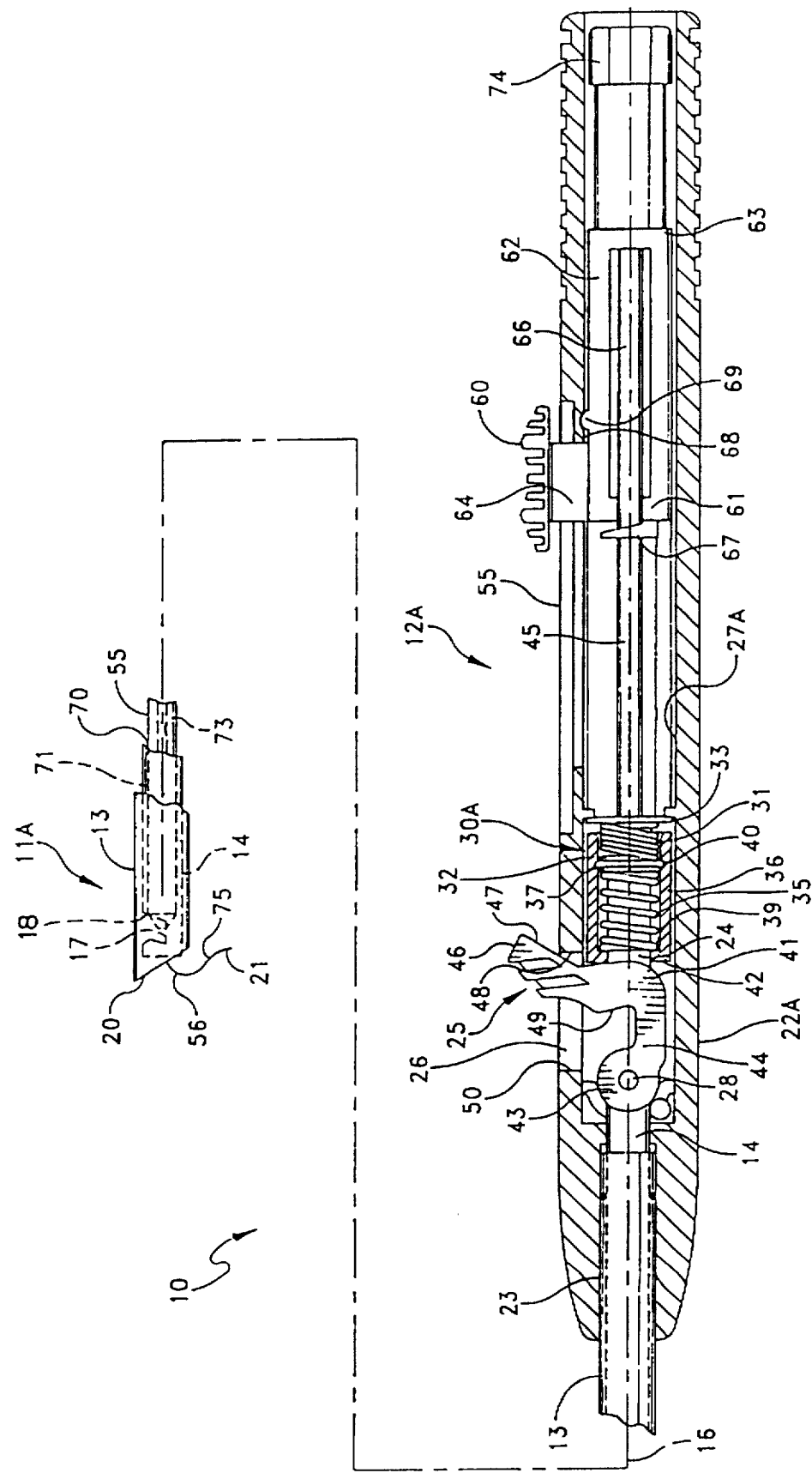
FIG. 8 is a view similar to FIG. 3, of a further embodiment of this invention.
Figure 9:
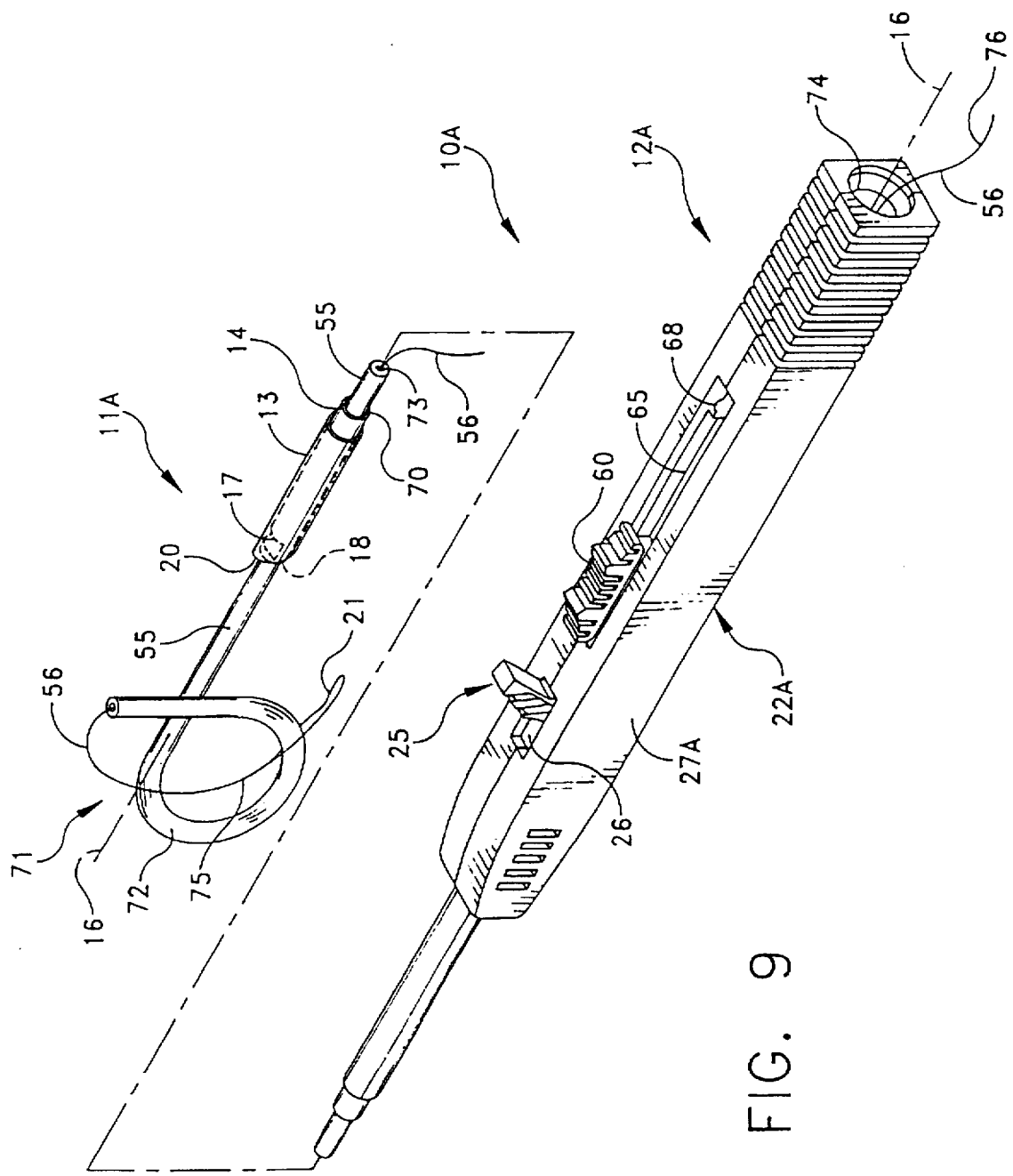
FIG. 9 is a perspective view of the embodiment of FIG. 8, with a second tubular member distally extending beyond the gripper members for facilitating intracorporeal knot tying.

Yet another needle grasping device 10A in accordance with this invention includes a proximal and distal sections 11A and 12A respectively as depicted in FIGS. 8 and 9. In FIG. 8 the gripper members, which include the slot 17 proximate the distal end 18 of the tubular member 14 and the distal end 20 of the sheath 13, operate in substantially the same fashion as the embodiment of FIGS. 1 through 4. The distal section further includes a catheter or second tubular member 55 for facilitating intracorporeal knot tying of the suture material 56, as further explained hereinafter.

With particular reference to FIG. 8, the proximal section 12A includes a handle 22A that supports the trigger 25 for operating the gripper members and apparatus for operating the first tubular member 14 substantially as described with respect to the embodiment of FIGS. 1 through 4. A slide 60 in the handle 22A connects with a base member 61 through an arm 62 extending distally from a slidable base 63 and an upstanding member 64 extending through a slot 65 in housing 27A of the handle 22A. The housing 27A slidably supports the base member 61 within a cavity 30A defined in the housing 27A. The base member also supports a proximal end section 66 of the second tubular member 55 on a second opposed distally extending arm 67. Thus displacement of the base member 61 responsive to movement of the slide 60 within the slot 65 urges corresponding axial displacement of the second tubular member 55. The handle 22A and the base member 61 includes corresponding detent members 68 and 69 for holding the base member 61 in the proximally retracted positions as illustrated in FIG. 8.

The second tubular member 55 that extends through a passage 70 in the tubular member 14 includes a distal end portion or bight 71 that is formed of a shape memory material. Thus, upon extension the bight 71 forms the loop 72 depicted in FIG. 9 and, as the bight 71 retracts into the tubular member 14, the bight 71 assumes the linearly extending condition depicted in FIG. 8. The second tubular member 55 includes a passage or lumen 73 (FIG. 8) for receiving the suture material 56 therethrough. A seen in FIG. 9, the suture material 56 preferably extends through a gas-tight seal 74 sealing a proximal end of the housing 27A. The device 10A as depicted in FIGS. 8 and 9 thus provides apparatus for both grasping the suture needle 21 as previously described with respect to the embodiments of FIGS. 1 through 3 and FIGS. 5 through 7 and for facilitating intracorporeal knot tying as described in U.S. Pat. No. 5,447,512 to Wilson et al. which is incorporated by reference herein.

That is, after removing the suture needle 21 from the slot 17 with a free end 75 of the suture material 56 secured to the suture needle extending distally of the bight 71 of the second tubular member 55, the operator extends the second tubular member 55 by operation of the slide 60 to extend the bight 71 relative to the sheath 13 and the tubular member 14 to form the loop 72. As described in U.S. Pat. No. 5,447,512 to Wilson et al., passing the free end 75 of the suture material 53 through the loop 72 forms a loose knot. Once a loose knot is formed, the operator grasps the free end 75 of the suture material 56 with forceps or other graspers (not shown), proximally displaces the slide switch 60, and proximally retracts a proximal end 76 of the suture material to tighten the loose knot and enable thereby the operator to form a suitable overhand knot. This process can be repeated as necessary. Thus it will be understood that the device 10A enables a user to employ the devices both for suture needle grasping and for intracorporeal knot tying.

Figure 10:
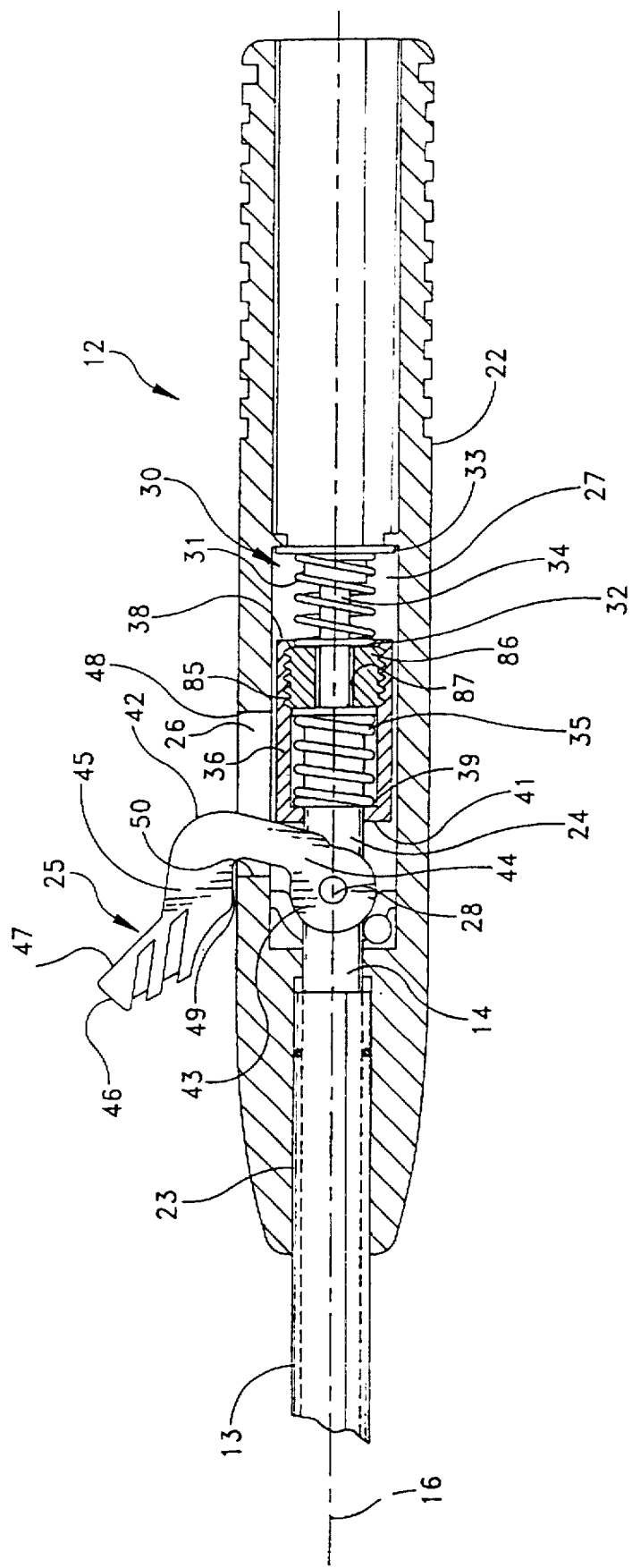
FIG. 10 is a view similar to FIG. 4 of another embodiment of the handle portion of this invention.

FIG. 10 illustrates an adjustable tension spring linkage 30 with spring cup 36 that includes a threaded portion 85 proximally of the groove 40 for threadably engaging a tensioning member 86 that includes an aperture 87 for receiving the guide tube 34 (FIG. 1). Adjusting the screw member 86 relative to the threaded portion 85 increases or decreases the tension in the spring 35 and hence the magnitude of the clamping force at the distal end 11 (FIG. 1). Those skilled in the art will appreciate that this adjustable lost motion transfer assembly 30 can be readily substituted for the assembly 30 of FIGS. 5 through 7 or the assembly 30 of FIGS. 1 through 4.

The foregoing embodiments depicted in FIGS. 1, 5, 8 and 10 satisfy the stated objects and aims of this invention. Each provides an apparatus for facilitating a modality of endoscopic therapy that includes a handle with operator means that includes a cam for axially displacing first and second tubular members to enable the grasping release of a suture needle. A device in accordance with this invention may also include apparatus for performing a second modality of therapeutic treatment in addition to needle grasping. The operator device can include portions for controlling the second modality of therapeutic treatment including the extension and retraction of a tubular member relative to the gripping members for facilitating intracorporeal knot tying of suture material extending through the apparatus.

The disclosed embodiments also provide a control or operator device, that positively retains the distal ends of axially extending members in selected open and in intermediate and fully closed positions depending upon interference between the axially extending members. Thus, the control device of this invention, with its function to extend and its lost-motion retraction of axially extending members may be used, for example, to extend and retract relative to a sheath a retrieval basket for retrieving stones and other items. That is, the handle portion of this invention can be used with a retrieval basket such as disclosed by U.S. Pat. No. 5,496,330 to Bates et al. and commonly assigned with this invention. In such case the lost motion assembly would enable extension and retraction of the basket relative to a sheath responsive to moving the trigger between its first and second positions. Thus, upon proximal retraction of the basket relative to an outer sheath with a stone larger than the sheath, the lost motion assembly would enable the basket and stone to be retracted against the sheath. The basket with the stone would be held in this intermediate position with the trigger in its second position due to the interference between the basket and stone and the sheath.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. In apparatus for facilitating endoscopic therapy having first and second axially, relatively displaceable coaxial members having proximal and distal ends and adjacent proximal and distal end portions wherein relative motion of the coaxial members defines first and second limit positions and, in response to interference between said end portions, an intermediate position, a handle means supporting the proximal portions of the first and second coaxial members for producing the motion between the first and second limit positions and to the intermediate position, said handle means comprising:

A. a housing attached to a proximal end portion of the first coaxial member;
   B. camming means supported in said housing for movement between first and second positions; and
   C. lost motion transfer means mounted coaxially with the coaxial members and concentrically with the coaxial members, abutting said housing, said camming means and the second coaxial member being responsive to motion of said camming means for producing motion to the first limit position when said camming means is at the first position and, when the camming means is at the second position, motion to one of the second limit position and intermediate depending upon the presence of interference between the distal end portions of said coaxial members.

2. Apparatus as recited in claim 1 wherein said lost motion transfer means comprises:
   i) cam follower means axially displaced from said camming means in said housing and mounted concentrically with the proximal end portions of the coaxial members;
   ii) first biasing means in said housing between said cam follower means and said housing for biasing said cam follower means toward the first limit position of said camming means; and
   iii) second biasing means in said housing means between said cam follower means and the proximal end of the second coaxial member for biasing the second coaxial member away from said camming means wherein said first biasing means compresses in response to motion of said camming means and said second biasing means compresses in response to motion of said camming means when an interference exists between the coaxial member.

3. Apparatus as recited in claim 2 wherein the distal end portions of the coaxial members include means for grasping a suture needle therebetween and the interference occurs when a suture needle is located in said grasping means, each of said first and second biasing means comprising a spring with said second biasing means spring have a greater spring modulus than said first biasing means.

4. Apparatus as recited in claim 3 wherein the second coaxial member includes an engaging surface on the formed proximal portion thereof and wherein said camming means includes a camming surface and said cam follower comprises an annular casing slidably supported with respect to the coaxial members, said casing having a skewed transverse member that interacts with the camming surface of said camming means and a transverse annular flange displaced axially from said skewed surface that provides a bearing surface for said first biasing means.

5. Apparatus as recited in claim 4 wherein the engaging surface on the second coaxial member comprises a radial flange and said second biasing means spring bears against said skewed transverse flange and the radial flange, said second biasing means spring compressing when said camming means moves between the first and second limit positions and a suture needle is located in the needle grasping means.

6. Apparatus as recited in claim 5 wherein said camming surface engages said casing, said biasing means causing said casing to maintain said camming means at one of first and second limit positions upon selective positioning of said camming surface in said first and second positions respectively.

7. Apparatus as recited in claim 3 wherein said coaxial members comprise an outer tube and an inner tube, said housing being attached to said outer tube whereby the inner tube moves relatively to the outer tube and the first limit, second limit and intermediate positions of the distal end of said inner tube constitute extended, retracted and suture needle clamping positions, wherein said camming means is positioned proximally of said cam follower means and both springs are expanded when said inner tube is in its extended position and said camming means is in its first limit position, wherein motion of said camming means to said second limit position displaces said cam follower means proximally to compress said first spring, said second spring being compressed as said camming means moves to the second limit position when said inner tube grasps a needle at the intermediate position.

8. Apparatus as recited in claim 7 wherein the second tubular member includes an engaging surface on the formed proximal portion thereof and wherein said camming means includes a camming surface and said cam follower comprises an annular casing slidably supported with respect to the coaxial members, said casing have a skewed transverse member that bears against the camming surface of said camming means and a transverse annular member displaced axially from said skewed surface for acting as a bearing surface for said first biasing means.

9. Apparatus as recited in claim 8 wherein the engaging surface on the second coaxial member comprises a radial flange and said second biasing means spring bears against said skewed transverse member and the radial flange, said second biasing means spring compressing when said camming means moves between the first and second limit positions and a suture needle is located in the needle grasping means.

10. Apparatus as recited in claim 9 wherein said camming surface engages said casing in an over center position when in each of the first and second limit positions of said camming means whereby said first and second springs urge said camming surface to remain in said first limit, second limit and intermediate positions upon selective positioning of said camming surface in said first and second limit positions respectively.

11. Apparatus as recited in claim 3 wherein said coaxial members comprise an outer tube and an inner tube, said housing being attached to said outer tube whereby the inner tube moves relatively to the outer tube and the first limit, second limit and intermediate positions of the distal end of said inner tube constitute retracted, extended and suture needle clamping positions, wherein said camming means is positioned distally of said cam follower means and both springs are expanded when said inner tube is in its retracted position and said camming means is in its first limit position, wherein motion of said camming means to its second limit position displaces said cam follower means proximally to compress said first spring, said second spring being compressed as said camming means moves to the second limit position when said inner tube grasps a needle at the intermediate position.

12. Apparatus as recited in claim 11 wherein the second tubular member includes an engaging surface on the formed proximal portion thereof and wherein said camming means includes a camming surface and said cam follower comprises an annular casing slidably supported with respect to the coaxial members, said casing having a skewed transverse member that interacts with the camming surface of said camming means and a transverse annular flange displaced axially from said skewed surface for acting as a bearing surface for said first biasing means.

13. Apparatus as recited in claim 12 wherein the engaging surface on the second coaxial member comprises a radial flange and said second biasing means spring bears against said skewed transverse flange and the radial flange, said second biasing means spring compressing when said camming means moves between the first and second positions and a suture needle is located in the needle grasping means.

14. Apparatus as recited in claim 13 wherein said camming surface engages said casing in an over center position when in each of the first and second limit positions of said camming means whereby said first and second springs urge said camming surface to remain in said first limit, second limit and intermediate positions upon selective positioning of said camming surface in said first and second limit positions respectively.

15. Apparatus as recited in claim 2 further characterized by coaxial catheter means further facilitating the endoscopic therapy and wherein said handle further includes means for displacing the catheter relative to the first and second tubular members.

16. Apparatus as recited in claim 2 wherein said housing includes a body portion defining a cavity therein and a passage extending through said body portion from said cavity, said camming means includes a first portion in said cavity for supporting said camming means and a second portion extending through said passage for enabling the displacement of said camming means between the first and second positions.

17. A needle grasping apparatus having proximal and distal ends for facilitating intercorporeal knot tying in suture material in an endoscopic procedure comprising:

A) first and second gripping means proximate the distal end of the apparatus with one of said first and second gripping means having a proximally extending actuating member for selectively gripping and releasing a suture needle;

B) catheter means extending between the proximal and distal ends of the apparatus for selectively extending and retracting relative to said gripping means for facilitating intercorporeal knot tying, said catheter means having a distal end portion defining a bight in the extended position and adapted for receiving suture material therethrough; and C) operating means for controlling said catheter means and first and second gripping means including:
 i) a housing attached to a proximal end portion of the first gripping means;
 ii) camming means supported in said housing for movement between first and second limit positions;
 iii) cam follower means axially displaced from said camming means in said housing and mounted concentrically with the proximal end portions of the gripping means;
 iv) first biasing means in said housing between said cam follower means and said housing for biasing said cam follower means toward the first limit position of said camming means; and
 v) second biasing means in said housing means between said cam follower means and the proximal end of the one of said first and second gripping means for biasing the proximal end of the one of said first and second gripping means away from said cam follower means wherein said first biasing means compresses in response to motion of said camming means and said second biasing means compresses in response to motion of said camming means when an interference exists between said first and second gripping means.

18. Apparatus as recited in claim 17 wherein said first and second gripping means includes an axially extending sheath and a coaxially extending member axially displaceable relative to the said sheath in response to said operating means, one gripper member being formed proximate a distal end of the sheath and the other of said gripper members being formed proximate a distal end of said extending member such that axial displacement of said extending member urges said gripper members between a suture needle gripping and a suture needle releasing positions.

19. Apparatus as recited in claim 17 wherein said catheter means extends within said coaxially extending member so that actuation of said operating means to axially displace said catheter means urges a distal end of said catheter means between an extended position distally of said first and second gripper members and a retracted position proximally of said first and second gripper members.

20. Apparatus as recited in claim 19 wherein said camming means includes a trigger for selective manipulation to urge axial displacement of said extending member relative to said sheath member and said operator means further includes slide means for urging the axial displacement of said catheter means relative to said sheath and extending members responsive to displacement of said slide means.

21. Apparatus as recited in claim 20 wherein said trigger includes a camming surface connecting with said coaxially extending member through said first biasing means so that manipulation of said trigger moves said camming surface relative to said extending member to urge thereby the axial displacement of said coaxially extending member.

22. Apparatus as recited in claim 21 wherein said slide means includes a base slidably supported in said operating means for sliding in the axial direction, said base engages said catheter means whereby manipulation of said slide means axially displace said base.

23. Apparatus as recited in claim 18 wherein said camming means includes a trigger for selective manipulation to urge axial displacement of said coaxially extending member relative to said sheath and said operator means further includes a slide switch to urge axial displacement of said catheter means relative to said sheath and coaxially extending member.

24. In apparatus having a proximal end and a distal end for selectively gripping a suture needle, said apparatus being characterized by introducer means that extend axially from the distal end of the apparatus, first and second gripper means proximate the distal end of the introducer means and supported for relative displacement between an open position to release a suture needle, an intermediate position to grasp a suture needle, and a closed position, an actuating member connected to and proximally extending from one of the gripper means, and handle means for supporting the introducer means proximally of said gripper means and for selectively displacing the actuating member to urge relative displacement of the first and second gripper means, wherein said handle means comprises:

A) a housing with an inner cavity;
B) camming means supported in said cavity for selective positioning by a user in an open position and a closed position;
C) first biasing means positioned in said cavity for urging the actuating member into engagement with said camming means; and
D) second biasing means supported in said cavity disposed in said cavity between a proximal end of the actuating member and said camming means for urging the proximal end of the actuating member away from said camming means such that said first and second biasing means maintain connection between said camming means and the actuating member upon positioning of the camming means whereby movement of said camming means in the open position urges the gripping means to the open position and positioning said camming means in the closed position urges the gripping members to one of the intermediate and closed positions depending upon the presence of a suture needle between the gripper means.

25. Apparatus as recited in claim 24 wherein the introducer means includes axially stiff, axially extending outer sheath with one of the gripper means defined at a distal end thereof and wherein said housing fixedly supports a proximal end of the sheath.

26. Apparatus as recited in claim 25 wherein the actuating member includes a tubular member coaxially extending with said sheath to carry the other of the gripper means, said other gripper means including a suture needle receiving slot formed in the tubular member proximate a distal end of the tubular member and wherein said housing supports the tubular member for axial displacement relative to said housing and said cavity receives a proximal end of the tubular member therein.

27. Apparatus as recited in claim 26 wherein said cavity includes a radially reduced interior diameter portion proximally of the proximal end of the tubular member and said first biasing means includes a coil spring extending between the proximal end of the tubular member and the reduced diameter portion such that said coil spring urges the tubular member toward said camming means.

28. Apparatus as recited in claim 27 wherein said second biasing means further includes a second coil spring overlying the tubular member, said second coil spring extending between said camming means and the proximal end of said tubular member such that said first and second springs urge connection between said camming means and the proximal end of said tubular member upon movement of said camming means between the open and closed positions.

29. Apparatus as recited in claim 28 wherein said first and second biasing means urges said camming means to remain in the open position and the closed position upon selective positioning of the camming means in the open position and the closed position, respectively.

30. Apparatus as recited in claim 24 further comprising catheter means for performing a second modality of treatment coaxially extending with the introducer means and wherein said handle means further includes a switch for displacing said catheter means relative to the introducer such that a distal end of the catheter means extends and retracts relative to the distal end of the introducer means.

31. Apparatus as recited in claim 30 wherein the catheter means includes a through lumen for receiving suture material, a distal section formed of a shape memory material for forming a loop upon extension from the introducer means and wherein said switch moves axially in said housing means and engages a proximal section of the catheter means such that distal displacement of said switch urges the distal section of the catheter means distally of the distal ends of the introducer means whereby the distal section of the catheter means forms the loop.

32. Apparatus as recited in claim 31 wherein the introducer means includes axially stiff, axially extending outer sheath with the one gripper means defined at a distal end thereof and wherein said housing fixedly supports a proximal end of the sheath.

33. Apparatus as recited in claim 32 wherein the actuating member includes a tubular member coaxially extending with said sheath and the one gripping member includes a suture needle receiving slot formed in the tubular member proximate a distal end of the tubular member and wherein said housing supports the tubular member for axial displacement relative to said housing and said cavity receives a proximal end of the tubular member therein.

34. Apparatus as recited in claim 33 wherein said cavity includes a radially reduced interior diameter portion proximally of the proximal end of the tubular member and said first biasing means includes a coil spring extending between the proximal end of the tubular member and the reduced diameter portion such that said coil spring urges the tubular member toward said camming means.

35. Apparatus as recited in claim 34 wherein said second biasing means further includes a second coil spring overlying the tubular member, said second coil spring extending between said camming means and the proximal end of said tubular member such that said first and second springs urge connection between said camming means and the proximal end of said tubular member upon movement of said camming means between the open and closed positions.

36. Apparatus as recited in claim 24 wherein said camming means includes a cam member and a cam follower abutting said cam member and wherein said first biasing means engages said housing and said cam follower to urge engagement between said cam member and said cam follower and said second biasing means engages said cam follower and a proximal end of the actuating member to urge the proximal end of the actuating member away from said camming member.

* * * * *

UNITED STATES PATENT AND TRADEMARK OFFICE
CERTIFICATE OF CORRECTION

PATENT NO. : 5,746,753

DATED : May 5, 1998

INVENTOR(S) : Roy H. Sullivan, et al

It is certified that error appears in the above-identified patent and that said Letters Patent is hereby corrected as shown below:

Claim 1, line 41, after "coaxial member" insert --, said lost motion transfer means--;

line 45, change "notion" to --motion--;

and line 46, after "intermediate" insert --positions--.

Claim 3, line 6, change "have" to --having--.

Claim 6, line 27, before "biasing", insert --first and second--.

UNITED STATES PATENT AND TRADEMARK OFFICE
CERTIFICATE OF CORRECTION

PATENT NO. : 5,746,753
DATED : May 5, 1998
INVENTOR(S) : Roy H. Sullivan et al.

It is certified that error appears in the above-identified patent and that said Letters Patent is hereby corrected as shown below:

Claim 8, line 53, change "have" to

--having--.

Signed and Sealed this

Eighth Day of September, 1998

Attest:

BRUCE LEHMAN

*Attesting Officer*     *Commissioner of Patents and Trademarks*